Figure 1:
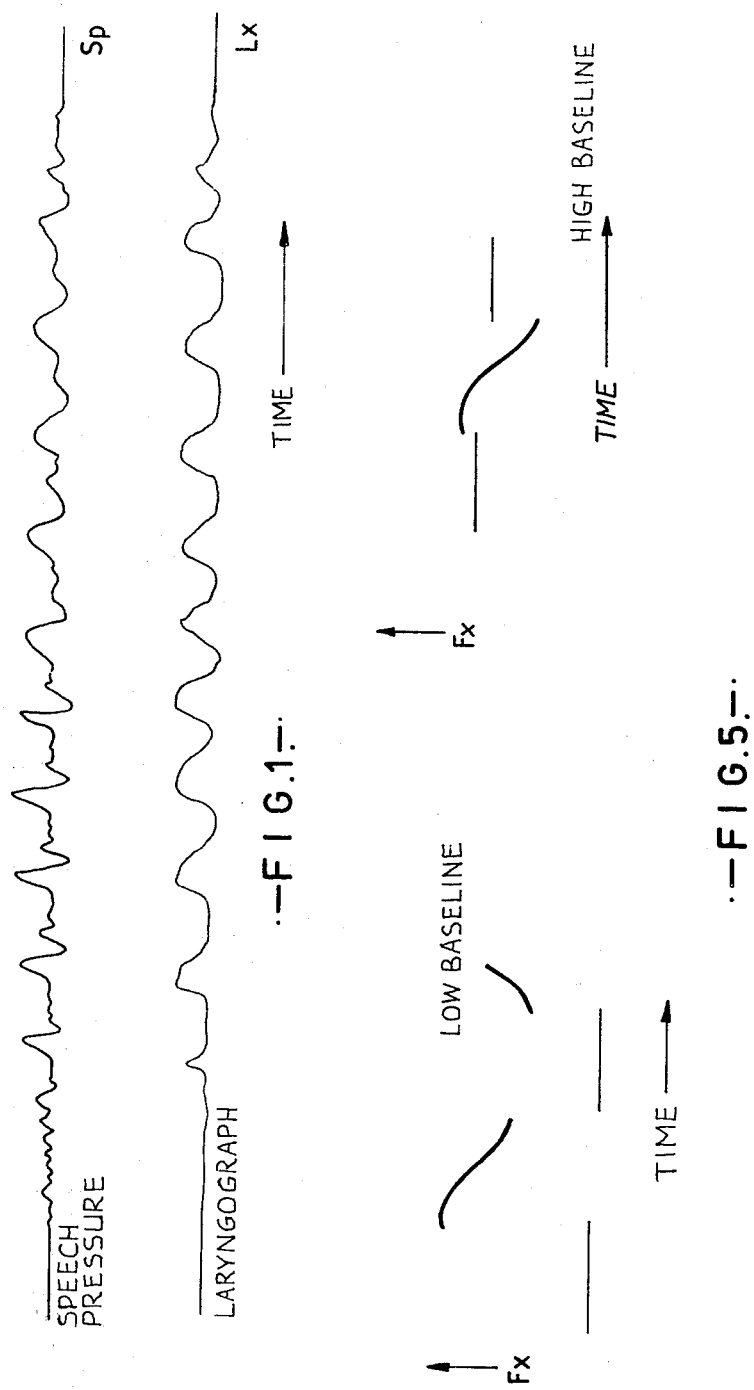

United States Patent [19]

Fourcin

[11] 4,139,732
[45] Feb. 13, 1979

[54] APPARATUS FOR SPEECH PATTERN DERIVATION

[75] Inventor: Adrian J. Fourcin, Hemel Hempstead, England

[73] Assignee: Larynogograph Limited, Hertfordshire, England

[21] Appl. No.: 866,843

[22] Filed: Jan. 4, 1978

Related U.S. Application Data

[63] Continuation-in-part of Ser. No. 650,628, Jan. 20, 1976, abandoned.

[30] Foreign Application Priority Data

Jan. 24, 1975 [GB] United Kingdom ............... 3269/75

[51] Int. Cl.$^2$ ........................ G10L 1/12; G09B 19/04
[52] U.S. Cl. .............................. 179/1 AL; 179/1 SC; 179/1 SP; 128/2.1 Z
[58] Field of Search ............... 179/1 AL, 1 SC, 1 SP; 128/2.1 Z, 2.5

[56] References Cited

U.S. PATENT DOCUMENTS

| 3,587,562 | 2/1968 | Williams | 128/2.06 |
| 3,677,261 | 7/1972 | Day | 128/2.1 Z |
| 3,871,359 | 3/1975 | Pacella | 128/2.1 Z |

OTHER PUBLICATIONS

Von Hippel, "Dielectric Materials", MIT Press, 1954, pp. 48, 50, 54, 57.

E. Nassimbene, "Speech Analyzing Circuitry", IBM Tech. Discl. Bull., Dec. 1963, p. 26.

*Primary Examiner*—Kathleen H. Claffy
*Assistant Examiner*—E. S. Kemeny
*Attorney, Agent, or Firm*—Edmund M. Jaskiewicz

[57] ABSTRACT

The invention relates to the monitoring, recording and display of a speaker's larynx waveform, for the purposes of education, speech therapy and speech analysis. A pair of electrodes are applied externally to the larynx region of the speaker's neck. Each electrode has two concentric surfaces (the outer surface is called a guard ring). One electrode feeds a carrier voltage to the speaker's neck. The other electrode receives the resultant larynx amplitude-modulated current. Detection techniques are used to derive the larynx waveform. A preferred detection technique is "slicing" which is herein defined as a demodulation which follows the changes in envelope of an amplitude-modulated carrier and retains only the small rapid larynx modulation filtering out the slower neck-movement modulation. The important feature of speech called intonation, which is made up of rhythm and pitch patterns, is directly correlated with larynx frequency. The present larynx waveform provides a simple and reliable basis both for the representation of intonation in speech and for the analysis of the frequencies defining other speech pattern features. Any combination of these patterns is displayed, on a domestic television receiver, for instance, and, or plotted or recorded.

15 Claims, 7 Drawing Figures

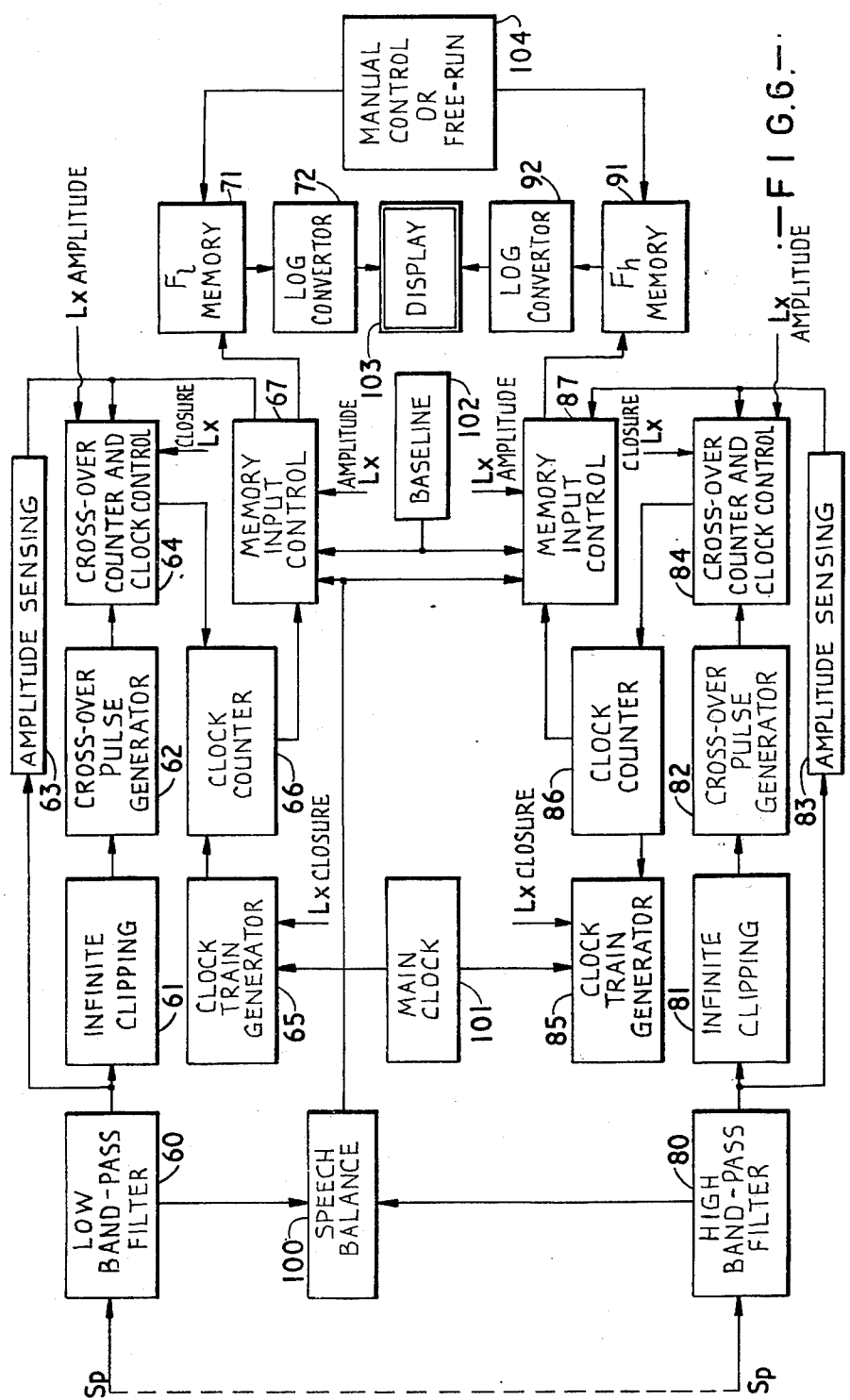

APPARATUS FOR SPEECH PATTERN DERIVATION

RELATED APPLICATION

This application is a continuation-in-part of the copending application Ser. No. 650 628 filed on Jan. 20, 1976, now abandoned by the same-named applicant.

The present invention relates to apparatus for use in the art of speech pattern derivation, and thus for instance may further relate to speech therapy, education and stress detection as in so-called "lie-detection". The following comments are offered by way of background information to the art with which the invention is concerned.

In the perception of speech we rely primarily on the analysis provided by the hearing mechanism to transform the complex variability of the acoustic signal into coherent slowly varying comprehensible patterns. A child's ability to perceive these patterns determines his progress in the acquisition of speech skills and an adult's ability to perceive new speech pattern forms determines the rapidity with which he acquires the speech forms of another language.

It is of advantage in teaching to provide for the immediate extraction of such pattern information from a speaker and his speech, the storage of such patterns and the instantaneous display thereof by visual, tactile or vibratile means to provide correcting or reinforcing feedback.

Any practical pattern teaching device must not only emulate the human hearing mechanism but also be economic and reliable. If the pattern analysis is based only on the acoustic form of speech it is impossible to reconcile these conflicting requirements since human auditory analysis involves a complexity of processing, even in its earlier stages, which is beyond the reach of present computational facilities.

This difficulty can be by-passed, however, when there is access to the speaker as well as to the acoustic form of his speech. In all languages the voiced sounds of speech play a more important part than all others, both in the earliest stages of speech development and in daily adult usage. Voicing is produced by the vibration of the vocal folds in the speaker's larynx and gives its intonation and pitch to the speaking and singing voice. The accurate instrumental analysis of the physical correlate of intonation, fundamental frequency, presents a major technical problem but if direct access to the voice producing vocal folds is possible then fundamental frequency determination and display is readily feasible. It is also possible to show the difference between a smooth, clear, vocal fold vibration and one which is rough and irregular. "Intonation", as defined in the dictionary, is the pattern or melody of pitch changes revealed in connected speech, particularly the pitch pattern of a sentence.

It is accordingly an object of the invention to provide practical means for the provision of such direct laryngeal access, an instrument suitable for the purpose being termed a laryngograph. The electrical output waveform from the laryngograph is herein termed Lx.

It is a further and subsidiary object to provide practical methods and means of deriving a fundamental frequency measure from this larynx information, of storing it in time-patterned form in a memory and of displaying this pattern both whilst the utterance from which it is derived proceeds and after it has ended. This fundamental frequency display or correlate of intonations is herein termed Fx. When used by a knowledgeable teacher this display of Fx can radically improve voice and intonation in the speech of a deaf person or a foreign learner and lends itself to subsequent selfteaching.

The invention is further concerned with the provision of means for the analysis, storage and immediate display, whether visual, tactile, or vibratile of speech sound quality information. Once the ability to reproduce and control voicing has been attained the learner must acquire and develop skill in the perception and production of the detailed sound differences between vowels, consonants, and their combination in words. In physical terms these differences reside in the temporal and spectral characteristics of the corresponding acoustic forms and we know from analysis and synthesis what are the main physical correlates of the perceptual pattern determinants of speech sounds. It is not at present possible to derive these physical pattern correlates in a way similar to that employed by the hearing mechanism, and accurate speech analysis is difficult and complex when it utilises only the acoustic signal.

There are two especially important problems in the acoustic analysis of speech. The first involves the discrimination of the voiced sounds from those which are produced in the speaker's vocal tract by a noisy turbulent air stream. The second involves the measurement of speech vocal tract resonant frequencies independently of the larynx vibration frequency. Both of these problems can be solved using a laryngograph-based analysis in which direct speaker access reduces the need for highly elaborate signal processing. Speech patterns can, in this way, be store-displayed in a way which corresponds to their auditory perception by relatively simple direct, and immediate, analysis; electronic storage here takes the place of auditory short term memory.

It has been proposed that a small electric current should be passed through a speaker's neck transversely at the level of the thyroid cartilage and voicing then associated with the corresponding modulation of the voltage appearing between the points of external electrical contact. This technique provides the basis for an external monitoring of the vibration of a speaker's vocal folds but it has not been widely used because of the extreme variability in its output, both for a single speaker over a period of time and for a variety of different speakers. To quite a good approximation, the equivalent electrical circuit of a speaker's neck, as connected above, is given by two impedances connected in parallel, Zn and Zl. Zn is the main neck impedance which is extremely low in comparison with Zl which is the vocal fold impedance. When a constant current is passed through this impedance arrangement, and $Zl > Zn$, then the resulting voltage is to a good approximation directly proportional to $(Zn - Zn^2/Zl)$. If a constant voltage is applied to this arrangement the resulting current is directly proportional to $(1/Zn + 1/Zl)$. The Zn component is not only highly variable from one speaker to another but also varies during the course of speaking as the supporting structures of the neck change slightly in position and differing laryngeal adjustments are made. It follows that the constant voltage arrangement is much to be preferred, since its output has the Zl component separated from the Zn component.

In addition, the use of a low impedance voltage source and of a low impedance current detector make it possible to use fully screened long leads, guard-ring electrodes, and isolating transformers so that the speaker is electrically isolated from any main equipment and his output shielded from interference.

According to the major aspect of the present invention, there is provided a laryngograph for the production of a larynx waveform, comprising a transmitting electrode and an oscillator for feeding a carrier input thereto, a receiving electrode for receiving the larynx-modulated carrier and means for detecting the larynx waveform from said received carrier. Techniques of carrier or amplitude slicing are conveniently used in processing the modulated carrier in order to implement a process of simple subtraction which then makes it possible to separate the smaller rapidly changing larynx component from the slowly varying neck component. The term "slicing" as used herein, is intended to mean demodulation which follows the changes in envelope of an amplitude-modulated carrier and retains only the small rapid modulation. This is especially useful when the envelope is small compared to the main carrier, since then only the wanted envelope remains for subsequent processing. However, it is envisaged that this result may also be obtained by other processing techniques and the present specification is not intended to be limited in this respect.

Slicing preserves only the top portion of the modulated carrier and, by a feedback process, substantially subtracts away the unwanted neck variations. The required larynx component is very small relative to the original carrier and slicing both reduces the final carrier component and keeps it largely constant so that the resulting modulated signal is within the dynamic range of the subsequent processing circuits.

Two different techniques of slicing control are possible; either by means of a feedback signal fed to a slicing circuit after derivation from the DC component of a low pass amplifier or by means of level control fed back to the oscillator driving the transmitting electrode. These methods may be used alternatively or in conjunction.

Advantageously, the electrodes used are formed from printed circuit boards, etched to produce a central circular element with a concentric ring spaced therefrom.

According to a preferred feature of the invention, means are provided whereby a correlate of intonation, is displayed, and/or recorded and/or plotted using memory techniques.

Figure 2:
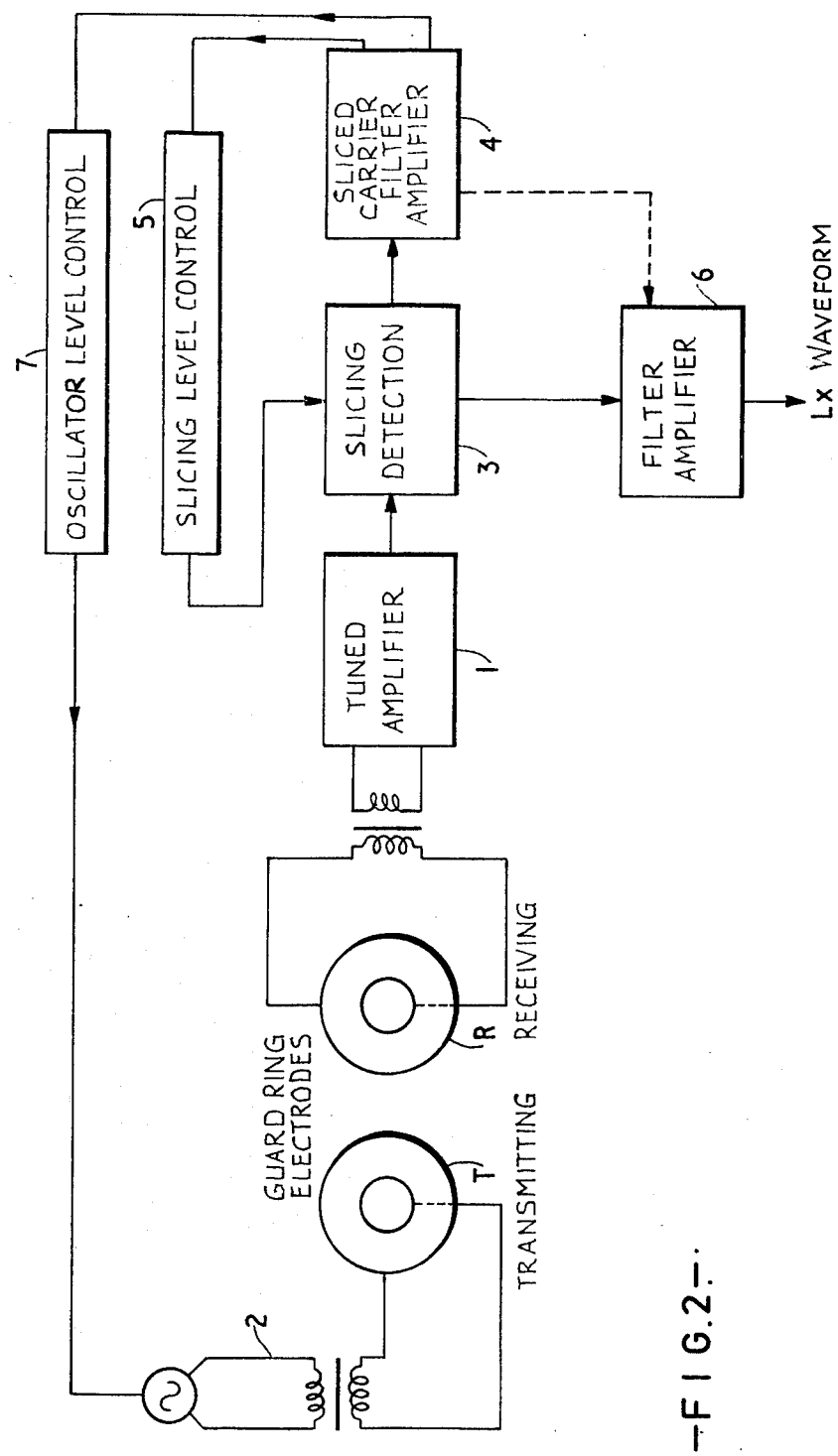
Figure 3:
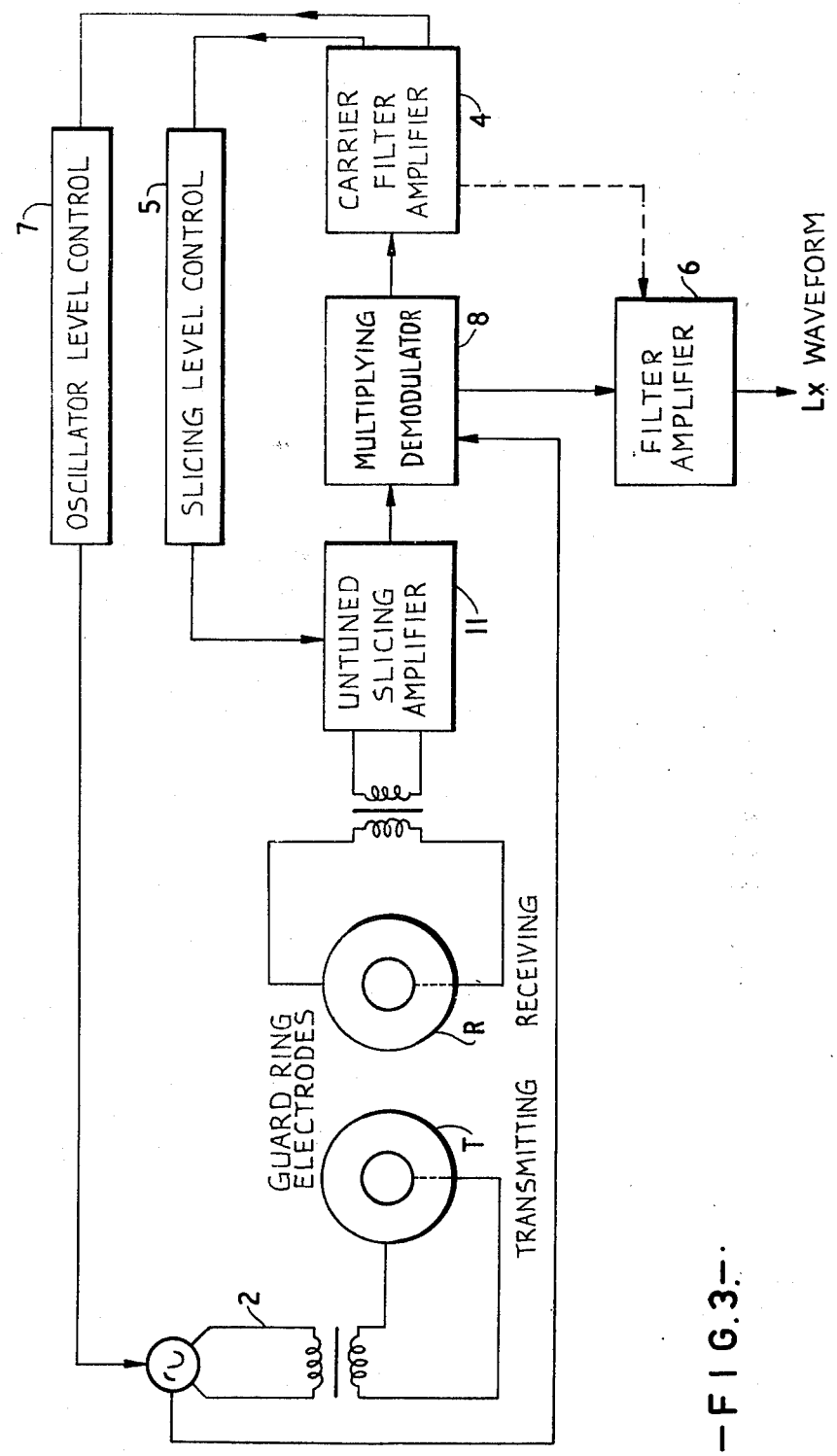
Figure 4:
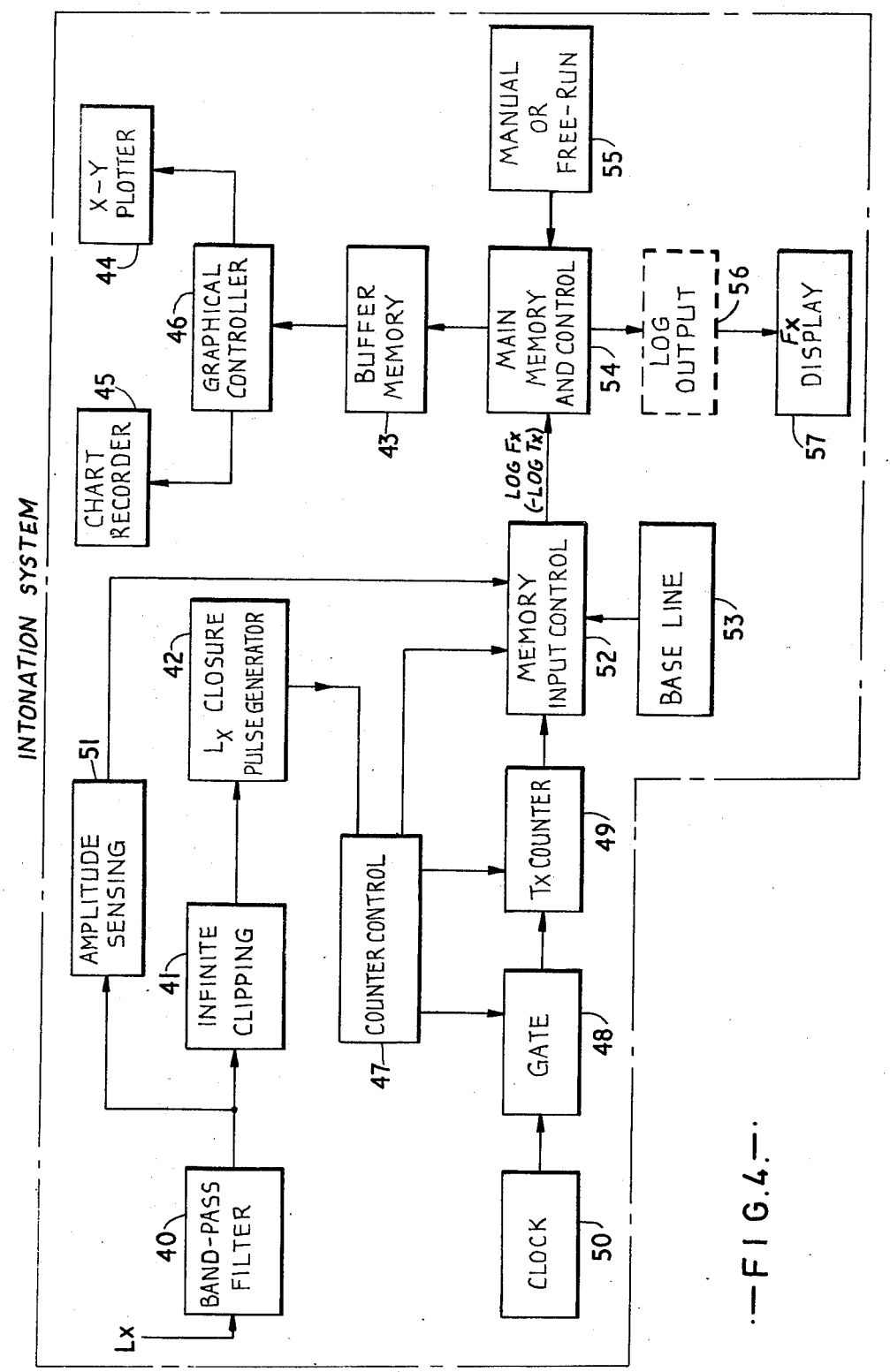
Figure 7:
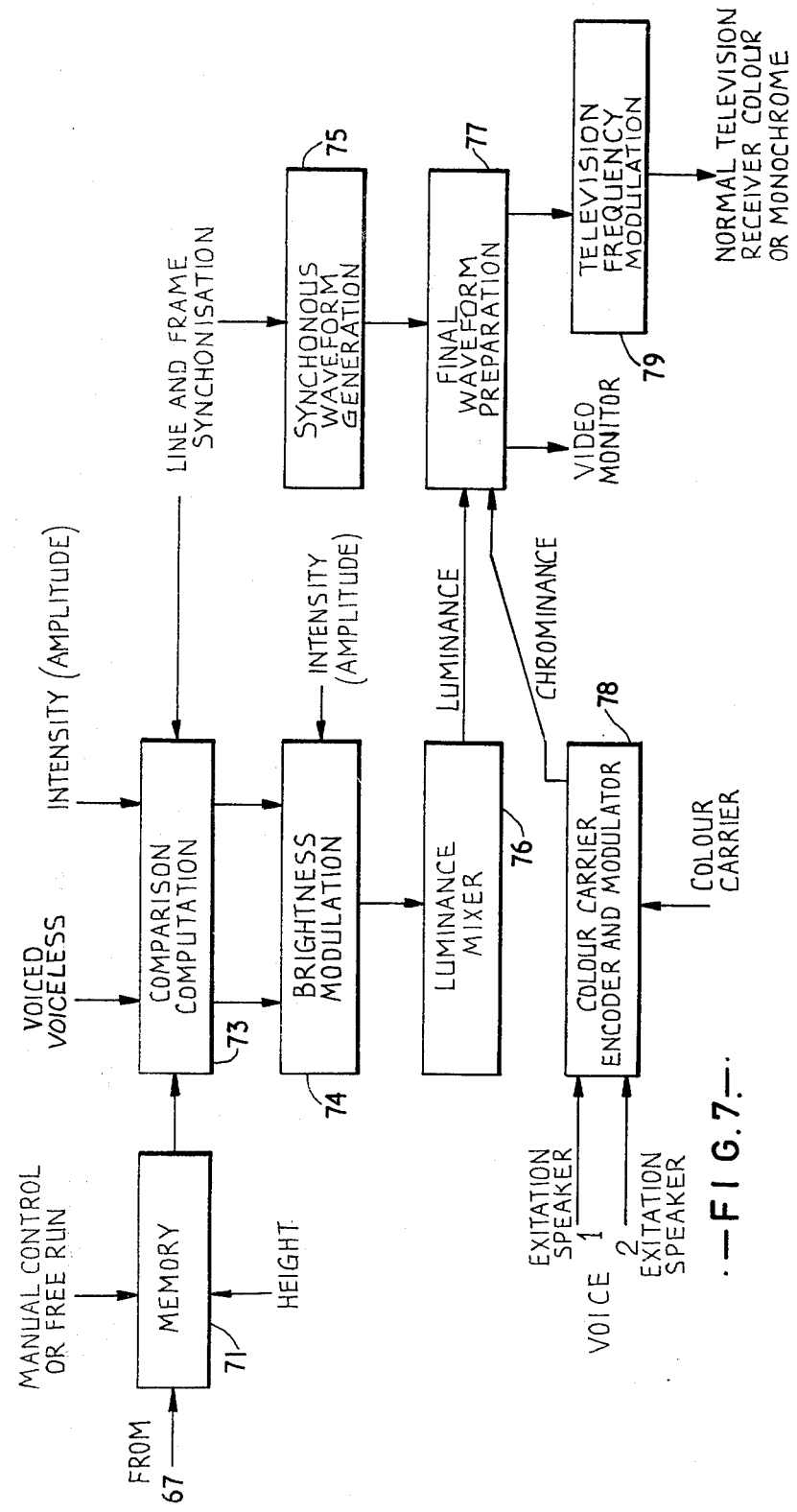

In order that the invention may be more readily understood, reference will now be made to the accompanying drawings which are given by way of example only and in which:

FIG. 1 shows in schematic form the vocal fold waveform information, Lx, obtainable from an electrical larynx vibration detector, herein called a laryngograph, FIG. 2 illustrates in block schematic form a first preferred arrangement for obtaining Lx waveforms, FIG. 3 illustrates an alternative arrangement for achieving the Lx waveform, FIG. 4 shows in block schematic form an intonation pattern, Fx, display generator, FIG. 5 shows two intonation plus baseline patterns, FIG. 6 shows, also in block schematic form, a speech sound pattern display generator, and FIG. 7 shows, illustrated in block schematic form, the television signal encoding of a speech sound pattern display.

In FIG. 1 there are shown speech pressure and laryngograph response waveforms. Only the voiced sounds in an utterance are responded to, and the response waveform Lx in FIG. 1, is largely independent of the speech pressure waveform, Sp.

Two arrangements for detecting the Lx waveform will now be described. FIG. 2 shows a tuned laryngograph with automatic carrier level controls and detection by slicing, and FIG. 3 shows an un-tuned laryngograph with automatic carrier level controls and detection by sliced multiplication. In both arrangements a transmitting guard-ring electrode T is driven by an oscillator 2 of low output impedance, preferably smaller than 10 Ohms, via an isolating transformer. No electrode jelly is needed, either for the transmitting electrode T or for a receiving electrode R, which is similarly connected to another isolating transformer. These transformers are important in securing complete electrical isolation for the wearer of the electrodes.

In the circuit of FIG. 2 the received signal is processed by amplifier 1 which is tuned to the same frequency as the oscillator 2, advantageously the frequency being between 500 KHz and 5 MHz. The amplifier 1 drives a detecting circuit in which only the top portion of the Lx modulated carrier is preserved. By arranging for this portion to be essentially invariant, apart from its Lx component, the variability due to changes in Zn (as hereinbefore defined) can be largely eliminated and the conditions of operation of the subsequent parts of the circuit maintained in spite of intrinsic speaker variability and change from one speaker to another. In the FIG. 2 embodiment, this top slicing is maintained constant by means of feedback to the slicing circuit. As shown, the feedback signal is derived from the DC component of a low pass amplifier stage 4, and fed via slicing level control 5 back to the detector 3.

The output of detector 3 may be filtered and amplified at 6 to provide the Lx waveform, or Lx may be obtained from 4.

An alternative or additional means of maintaining the top slicing constant, comprises the provision of a level control 7 for the oscillator 2 derived, like the feedback signal, from the amplifier 4. In FIG. 2 both slicing control systems are shown incorporated in the same embodiment, but it is to be noted that the two systems may be used separately and alternatively. The first system has a theoretical advantage, however, since it involves no control signal modulation of the larynx output.

In practical use of the laryngograph, interference may be produced by broadcasting transmitters using the same frequency or by other RF apparatus, for example diathermy equipment in a hospital. The reception of such interference by the arrangement of FIG. 2 may render it necessary to change the frequency of operation by retuning. Although this is possible, an easier approach to the problem is afforded by the arrangement of FIG. 3, with which it is necessary only to change the frequency of operation of the oscillator. Where applicable like reference numerals are utilised for like parts in FIGS. 2 and 3, the arrangement of FIG. 3 differing from that of FIG. 2 mainly only in the manner of modulation detection.

As shown in FIG. 3, a broad band, or untuned slicing amplifier 11 feeds a multiplying demodulator 8, which in turn feeds carrier filter amplifier 4 and filter amplifier 6. Whereas feedback control in the circuit of FIG. 2 is between units 4 and 3 via unit 5, in the circuit of FIG. 3 it is via unit 5 between units 4 and 11, with a feed connection also from the oscillator 2 to demodulator 8. Oscillator level control is again shown at 4, 7, 2. The laryngograph is especially suitable for this type of signal processing because the transmitting source can be made directly available to the receiving circuits.

Slicing, as carried out in the present application and illustrated in FIGS. 2 and 3 retains the desired larynx modulation, due to Zl, and discards the unwanted slow-neck modulation Zn (Supra Page 5). The level of slicing is altered to obtain desired modulation. A particular circuit arrangement for the detection of an amplitude modulated carrier and the derivation of an automatic volume control signal from the filtered rectified carrier is shown in FIG. 10-2 in the Standard Reference Textbook "Radio Engineering" by F. E. Terman, McGraw-Hill (1947) on Page 505. Basic waveforms relative to amplitude modulation and detection by rectification are shown in FIGS. 1-2 in Terman. FIGS. 10–22$b$ in Terman shows how a carrier may be rectified with bias so that the top part of the waveform is sliced off. In FIG. 2 of the present invention, this bias is obtained from the amplifier 4 and is fed back by slicing level control 5 back to the detector 3. In FIG. 3 of this application the same basic arrangement is used except that the output of slicing level control 5 controls slicing in the amplifier 11.

In use of both the arrangements of FIGS. 2 and 3, identical transmitting and receiving electrodes T, R are used, and about 3 V. r.m.s. are maximally applied to the transmitting electrode. A convenient and preferred electrode construction which is comfortable to wear and electrically functional is based on the use of a standard printed circuit board which is etched to produce a central circular element (which may optionally be pierced) of about 17 mm overall diameter with a concentric ring spaced therefrom by 3mm and 5mm wide. This may be formed from the board by a conventional punch and die on a fly-press. A double sided printed circuit board with plated through connections may advantageously be used, with the reverse side providing an earth screen and a soldered anchoring for cables.

It is here convenient to note that the signal derived from the laryngograph, Lx, is useful for the following reasons:

(1) it gives information about the nature and timing of vocal fold contact without interfering with the speaker or his speech; this may be used in the teaching of speech and language skills;

(2) disorders of the vocal folds and of speech itself have characteristic correlates in the Lx signal and these features may be used in diagnosis;

(3) the laryngograph signal may be directly and indirectly used to produce voice-like sounds for research and for entertainment. Typically closure will be detected in each cycle and derived signals will be produced from the closure timing but Lx may be used directly or via circuit processing to provide an immediate auditory stimulation or an input for recording;

(4) the visual, tactile or vibratory presentation of Lx to a subject may be used in the teaching of voice production;

(5) the immunity of Lx to acoustic noise provides the basis for an ideal voicing detector and makes it possible for novel and effective methods of speech transmission to be based on its use.

Once the Lx waveform has been produced at the output of the filter amplifier 6, it is possible to make analyses of speech which are normally difficult and even acoustically impossible. The methods involved depend essentially on two operations.

The first operation involves the use of Lx to detect the presence of speech perceptible larynx vibration. Since vocal fold closure is necessary to the production of a good voiced sound, and since Lx is only obtained from vocal fold closure, Lx provides an excellent indication of voicing with which no acoustic disturbance or internal vocal tract noise can interfere.

The second operation makes use of the extreme reliability of the sharp rise in the Lx waveform as an indicator of vocal fold closure. This Lx rise provides an exact indication of the beginning of each vocal fold cycle.

From FIG. 4 there may be gained a better understanding of the application of these operations in the method used for the derivation, display and recording of intonation.

The Lx signal is band-pass filtered at 40, the signal arriving either directly from a laryngograph (not shown) or from a laryngograph recording made during a speech utterance.

Partial amplitude clipping of Lx and subsequent full wave rectification in 51 will produce a signal which can be smoothed with a time constant of only a few milliseconds to give a good indication of voicing. This smoothed signal will not be unduly influenced by peaks in vocal fold activity but will nevertheless be sensitive to the onset and tail of larynx vibration in utterances, and be capable of setting and resetting a bistable circuit to indicate the presence or absence of voicing in a control to standard logic circuits. This voicing indicator can be used to prevent false larynx pulses from giving spurious information. In FIG. 4 infinite clipping is effected at 41, and a uniform pulse is accurately placed by generator 42 for each larynx closure. This generated pulse can be used to control standard logic circuits to give the basis for measuring vocal fold vibration period, Tx. Frequency is of course the reciprocal of period and Tx thus defines Fx, so log Fx = − Log Tx.

In FIG. 4 there are shown means whereby temporally uniform, or non-uniform, clock pulse trains, from 50 via 48, may be counted in 49 to give a measure of Tx which can be stored via 52 in a recycling or alternatively a random access memory, 54. The final display of Fx by 57 is best presented on a logarithmic scale and if uniform clock pulse spacing is used the output from the memory must be logarithmically converted in 56 after digital to analogue conversion. If a suitable non-linearity of clock pulse spacing is used this logarithmic conversion, or indeed any other which is desirable, may be accomplished in the Tx counter 49, prior to memory storage and 56 need only be concerned with analogue conversion. The display, 57, may occur with advantage as the input speech, and its accompanying Lx, proceed. The speaker may then be taught to modify and correct his speech with immediate reference to the displayed pattern. The arrangement for generating a stored Fx display from Lx information, which is disclosed in FIG. 4, may easily be associated with simple known means for the extraction and display of speech intensity or amplitude information. Although Fx provides the primary physical correlate of stress, amplitude, which is the physical correlate of loudness, is also of importance in stress perception. Simple known ways of amplitude envelope extraction are available and this signal may be packed with the Fx words (in the computer sense) in the memory and used in the display to brighten and or widen the trace, and or change the colour of the display.

As the display proceeds from left to right it is a considerable advantage, when a visual presentation is used, for the silent and unvoiced portions of speech to be represented by a baseline which moves horizontally across the display at a constant height. The baseline generator 53, not only serves as a place marker in time but it may also be used in teaching to provide a pitch-height target when it is made adjustable. This is illustrated in FIG. 5 where the same utterance is shown in relation to two baseline heights. The presentation may be automatically recycled for the learner's successive attempts or under manual control 55. It is also possible for a tape recorded model to be available to the learner with speech on one track and Lx, to give Fx, on the other. This tape can also be arranged to control the display by the use of a precursive tone or code signal which erases the memory and re-triggers the memory and display sequence in the manner of 55.

The use of a digital memory and associated digital logic circuits provides both a high degree of reliability and the possibility of further processing by means not shown. In the specific embodiment of FIG. 4 there is shown means for controlling a chart recorder 45, or x-y plotter 44. As such means 46 are well known in the art no detailed description is given herein. However it is noted that the use of a buffer memory 43, makes it possible to provide a complete plotting control so that only voiced segments of the speech are drawn slowly and accurately while intervening voiceless or silent pauses are moved over quickly with the pen raised.

For the deaf, speech skills which depend on the control of breathing, timing and the dynamic adjustment of the vocal folds can be better taught with the laryngograph based display than with any other technique. This approach is not especially useful, however, in the teaching of those speech skills which depend on articulatory control. The precise adjustment of the speaker's lips, tongue, soft palate and pharynx are also necessary in order to achieve a sufficient definition of the sounds of speech. The success of the intonation display stems from its ability to provide a direct correlate with the perceptual patterning of pitch, rhythm and voice quality. It is this provision of a feedback to ensure that the speech produced is perceptually acceptable which is basic to the operation of the arrangement for sound quality display which is shown in FIG. 6. Here salient auditory pattern features in speech sound discrimination are analysed, stored and displayed in the immediate feedback manner which characterises the operation of the intonation display of FIG. 4, using both speech and Lx waveforms as inputs.

The ready definition, using Lx, of both whether voicing occurs and at what instant a laryngeal excitation pulse is generated facilates the analysis of speech patterns. The arrangement of FIG. 6 provides for the time course of the characteristic frequency in two frequency bands Fl, and Fh, to be shown on a stored display with a distinction being possible between parts of an utterance which are voiced, fricative or voiced-fricative in form. These distinctions are based on the combined use of speech filtering and Lx amplitude sensing, using the previously described amplitude sensor, and the Lx amplitude information which is available from the arrangement of FIG. 4. A speech balance circuit gives an output when there is greater energy in the high frequency band than in the low and this enables voiced fricatives to be detected when Lx is present.

In one preferred embodiment, instanced by way of non-limiting example the Fl band extends up to 1kHz and Fh extends above 1kHz. Alternatively, the Fl band may be based on a low-frequency emphasis of 6 dB/octave and the Fh band based on a high-frequency emphasis of 8dB/octave. Other approaches may however be adopted. The determination of the characteristic frequency in each of the two bands is preferably arranged by counting the time which elapses for a fixed number of zero crossings to occur after the occurrence of an Lx closure pulse. This time may be counted with a uniform or non-uniform clock pulse train to arrange for the requisite scaling of the final display, as above when the physical correlate of intonation was being processed, or again as before, final logarithmic or similar shaping may be used prior to actual display. In speech production a finite time is required for the acoustic disturbance initiated by a laryngeal closure to be propagated along the vocal tract and from the speaker to a microphone. In consequence, it is necessary to delay the binary Lx closure information before using it in the processing of the speech waveform. The delay used in each case may be slightly increased to allow for the propagation of the band pass filtering. A small difference in delay adjustment is desirable, but not essential, in order to cater for the differences which exist between vocal tract lengths - "Adult" and "Child" settings may be used.

In this way there is no interference between voice frequency and vocal tract frequency and there will not be a spurious display of harmonics of the fundamental frequency of voiced sounds. Unvoiced, fricative, sounds are analysed at a fixed rate which may be determined either by their rate of producing zero crossings or by an interval timer. Both of these arrangements are feasible but the former is preferable.

The essential details of a speech pattern display of this type are shown in FIG. 6. The elements contained in this figure are symmetrically disposed with the same main functions shown above a line running through the common components 100, 101, 102, 103, and 104, also occurring below. The top half of the arrangement provides a pattern line for Fl, the low-frequency component, whilst the lower half gives a pattern line for Fh, the high-frequency pattern component. In the derivation of the Fl line the first processing steps 60, 61 and 62 in FIG. 6, starting from a speech waveform input, are similar to 40, 41 and 42 for the derivation of an intonation pattern from Lx in FIG. 4. By arranging for the time interval associated with a fixed number of zero crossing pulses following an Lx closure, when there is a detected Lx amplitude to be determined, using 64, 65 and 66, an input to digital memory, 71, can be provided with corresponds to Tl. The counting of this low characteristic period, Tl, and of the high characteristic period Th, provides the basis for determining log Fl and log Fh by the use of Lx triggered log time scaling in the output from 65 in counting with 66, or alternatively by the use of log conversion, in 72 and 92, immediately prior to display. A logarithmic scale is preferably here, as it is for the Fx correlate of intonation, because it corresponds well with our perception of speech patterns, and facilitates a conversion from Tl and Th to Fl and Fh.

If a purely fricative sound is produced there will be no Lx amplitude and 64 and 84 will operate in a regular sampling mode in which crossing counts are initiated at a fixed time interval rather than by Lx closures. This fricative information is encoded in memories 71 and 91 by the respective memory input control units 67 and 87. If, however, the speaker produces a voiced fricative then fricative energy will be detected in the high band pass filter output, 80 and this will result in an output from 100, but there will also be an appreciable Lx amplitude signal. This information can also be encoded by 67 in the memory 71.

Two other important sound classes are catered for. Nasal consonants may have voiced energy only in the low frequencies. In this event 63 will signal the presence of a component but 83 will not; in consequence only the Fl line will be displayed. Following voiceless plosives the onset of voicing may have little energy and there may be little friction in the low frequencies, this will result in the suppression of the Fl line by the low output from 63. Fh, however, will be shown since there will be an output from 83. Whispered speech will similarly have its main pattern features shown, there will merely be a switch from a voiced to a voiceless mode of display.

The final display may be stored repetitively or maintained for one utterance by the control of the recirculating or random memory. The memory itself is digital and may be synchronised both with that for the other speech frequency and with that for the intonation display. In addition to storing the information basic to the specification of log Fl and log Fh each of the memories will store, for each displayed point, details of the excitation. Two bits extra for each Fl point are needed; one to specify voiced or unvoiced and the other to specify the presence of a voiced fricative. Only one bit is needed in Fh to specify voiced or unvoiced. The range of Fh is greater than that of Fl and this disparity in bit representation, if identical stores are used, will not vitiate the displays. Additional bits in each of the stored words in both the Fl memory, 71, and the Fh memory 91, may be assigned to represent respectively the amplitude envelope signals derivable from the low band-pass filter, 60, and the high band-pass filter 80. This information may then be used to control the type of Fl and Fh display which is provided by, for example, controlling the width and or brightness and colour of the visible lines.

For a visual display, the different conditions of vocal tract excitation and the difference between Fl and Fh patterning may be conveniently shown by the use of colour. For example, the voiceless, fricative, sounds may be shown in white; Fx is green, which corresponds to the p31 phosphor of a simple display; Fh in red and Fl in blue. Voiced friction may then be conveniently denoted by a reduction in colour saturation.

A modern colour television receiver is an especially appropriate device for this type of display since it is relatively inexpensive, generally available and provides a sufficient degree of picture resolution for the differences between speech patterns to be readily distinguished. In addition, however, the availability of video recorders in the home, school and hospital clinic makes it possible to give instruction in the use of the apparatus with the same television display which is used for live pattern presentation.

A further advantage of a television display comes from the relative ease with which it can be interfaced to the circuits typically used for pattern derivation in FIGS. 4 and 6. In FIG. 6, for example, the low characteristic frequency pattern information, Fl, is stored in 71. The sequential (e.g. shift register) version of the digital memory 71, can be used in conjunction with a standard television display by arranging for the timing of one complete memory sequence to correspond to the line period of the television raster. When the content of each binary memory word is then compared with the binary representation of the line number on the raster it is easy for those who are familiar with standard digital and television techniques to arrange for the stored pattern in the memory to appear as a series of bright points forming a line on the television screen. In this way, position from left to right on the screen is controlled by the temporal occurrence of a stored binary word in the memory sequence, and the position from top to bottom of the screen at which a point is brightened is determined by the content of the stored binary word in FIG. 6, 71, memory sequence. A specific numerical example will clarify this display scheme; eight bits in each of the memory words makes it possible to select any one of 256 lines in a vertical sense; if the line period and the memory sequence period are both 64 $\mu$s and the memory clock rate is 8 MHz then 512 separate points may be represented horizontally.

The range of raster lines devoted to any particular speech pattern feature, Lx, Fl or Fh, is determined by the clock train generator, 65 in FIG. 6 for Fl, and this generator also provides the basis for the shaping of the transfer characteristic. It is not a very practical arrangement to use a logarithmic convertor after the memory store. The height of the displayed pattern must also be controlled digitally and this is readily achieved by the addition of a binary number to the circulating memory words. The provision of a height control is the only major source of difference between the memory 71 in FIG. 6 and that shown as 71 in FIG. 7.

In FIG. 7, the elements 71, 73, 74 and 76 are concerned only with the interfacing of the Fl pattern line to the television display; it is to be understood that similar, additional, elements are needed for each extra pattern feature which is to be displayed. In order to select the line and time at which a pattern point is displayed the Fl content of each word in 71 must be compared with the current raster line number and 73 is intended, in part, to make this comparison computation. In addition, however, the comparison effected in 73 makes it possible to control the width of the final displayed pattern by controlling the range of raster lines for which a particular Fl will be represented on the display. In this way an unvoiced sound is made vertically wider than a voiced fricative and a voiced fricative made wider vertically than the representation for a purely voiced sound. Similarly it is possible to arrange for Fh, Fl and Fx to be given different widths in the final display, Element 74 in FIG. 7 makes it possible to control the luminance of the display as a function of sound pattern intensity and as a function of the nature of the pattern and its excitation.

It is important to note that these modulations of width and brightness operate only on the luminance component of the final pattern. In consequence they are of equal importance in both monochrome and colour television speech sound pattern displays and an intrinsic compatibility between the two types of display is thus obtained. In addition, a colour blind learner, or teacher, can operate with complete efficiency since the additional use of colour, although desirable, is redundant.

Colour information is best derived from the type of pattern line displayed and whether the speech excitation for this pattern line is voiced, voiceless or a combination of these two. In the absence of sound a neutral or black background will be shown. This excitation information is encoded with the main pattern information in each memory word and it is used in element 78 as well as in element 73 in FIG. 7. Quite straightforward modulation techniques are used in 78 in order to prepare the colour signal for incorporation into the final video waveform in 77. The luminance signal from 74 could be connected directly to 77 if only one pattern feature were to be shown but, normally, additional patterns from the same speech source must be displayed to form a family of patterns and the simultaneous display of the family from, for example, the teacher must be catered for. The necessary mixing of these several signals is accomplished in 76.

The final output of 77 may be used as a direct link to a video monitor and as a source of modulation to a television frequency carrier, in 79. The output of 79 can then be used in the same way as the signal from a television antenna.

The brightness and width information associated with Fh and Fl visual displays may also be used in tactile and vibratile displays to signal the voiced, voiceless fricative and voiced fricative excitation qualities. The Fl and Fh patterns may be fed to arrays of transducers in this situation so that a complete but simple speech sound pattern representation is available to the wearer. It is not essential here to use a memory and these may be eliminated from the arrangements shown in FIGS. 4 and 6.

We claim:

1. A laryngograph for the production of larynx closure signals, without interfering with the speech of the speaker comprising a first low impedance circuit with a transmitting electrode and an oscillator for feeding a carrier voltage input signal thereto, a second low impedance circuit with a receiving electrode for receiving a larynx-modulated carrier current output signal, said transmitting and receiving electrodes adapted for positioning in firm and continuous skin surface contact opposed from each other on the neck of a speaker, means on said electrodes for reducing the travel of electric current across the surface of the skin on the neck, means for detecting the larynx closure signal from said received carrier current, and means, connected to said detecting means, for producing signals representative of the associated speech patterns.

2. A laryngograph according to claim 1, wherein the detecting means comprises means for slicing the carrier to implement subtraction for detection of the waveform from the carrier.

3. A laryngograph according to claim 2, wherein the slicing means comprises a slicing circuit and low pass amplifier, and means for feeding a feedback signal to the slicing circuit after derivation from a DC component of the low-pass amplifier, to achieve slicing control.

4. A laryngograph according to claim 2, and comprising level control means connected to said detecting means for generating a level control signal fed back to the oscillator driving the transmitting electrode circuit to effect slicing control.

5. A laryngograph according to claim 2, wherein said detecting means comprises a slicing circuit, a low pass amplifier connected to said slicing circuit and generating a feedback signal fed to the slicing circuit after derivation from a DC component of the low-pass amplifier, for slicing control, and level control means connected to said detecting means for generating a level control signal fed back to the oscillator driving the transmitting electrode circuit for further slicing control.

6. A laryngograph according to claim 2, comprising a broad band untuned slicing amplifier connected to said receiving electrode circuit, a multiplying demodulator fed by said slicing amplifier and a carrier filter amplifier and a filter amplifier fed by said demodulator, a slicing level control connected to said carrier filter amplifier to provide feedback control between the carrier filter amplifier and untuned slicing amplifier and an oscillator level control between the oscillator and demodulator.

7. A laryngograph according to claim 1, wherein the electrodes are formed from printed circuit boards, etched to produce a central circular element with a concentric ring spaced therefrom.

8. A laryngograph according to claim 1 and further comprising processing means for deriving a correlate of intonation by fundamental frequency measurement from a larynx waveform, said processing means comprising a band pass filter and amplitude sensing means fed by said band pass filter, in parallel with infinite clipping means which feed a pulse generator, said generator producing uniform pulses for each larynx closure and said pulses being fed to control means operative on a clock pulse generator associated logic circuitry feeding to display.

9. A laryngograph according to claim 8, whrein said control means comprises counting means for counting clock pulse trains from said clock pulse generator and digital memory means to store the count measure.

10. A laryngograph according to claim 9 and comprising display means connected to said control means for display of the said stored clock count measure.

11. A laryngograph according to claim 10, wherein the display means comprise a logarithmic scale and digital to analogue conversion means for converting clock counts into logarithmic units.

12. A laryngograph according to claim 8, further comprising a plotter, control, and a buffer memory to provide plotting control so that only voiced segments of speech are measured and drawn slowly and accurately while intervening voiceless or silent pauses are moved over quickly.

13. A laryngograph according to claim 1 and further comprising processing means for deriving low and high frequency pattern with line components from a speech waveform from a microphone, said processing means comprising means for deriving a pattern line for a low frequency component and a pattern line for a high frequency component; the means for deriving the low frequency line comprise a low band pass filter, amplitude sensing means and infinite clipping means, in association with a digital memory, and the means for deriving the high frequency line comprise a high band pass filter, amplitude sensing means and infinite clipping means, in association with a further digital memory.

14. A laryngograph according to claim 1, and further comprising processing means for deriving a correlate of intonation by fundamental frequency measurement and low and high frequency pattern line components from a speech waveform from a microphone, said processing means comprising a band pass filter and amplitude sensing means fed by said band pass filter in parallel with infinite clipping means which feed a pulse generator, said generator producing uniform pulses for each larynx closure and said pulses being fed to control means operative on logic circuitry; said processing means further comprising a low band pass filter, amplitude sensing means and infinite clipping means in association with a digital memory; and said processing still further comprising a high band pass filter, amplitude sensing means and infinite clipping means in association with a further digital memory.

15. A method of producing a larynx waveform, comprising the steps of feeding a carrier voltage signal into the area of the larynx of a subject, receiving the larynx-modulated carrier current and detecting the larynx waveform from said received larynx-modulated carrier current, and further comprising the step of processing and displaying the detected larynx waveform.

* * * * *